United States Patent
Jacobsen et al.

(10) Patent No.: US 6,997,937 B2
(45) Date of Patent: Feb. 14, 2006

(54) DETACHABLE COIL FOR ANEURYSM THERAPY

(75) Inventors: Stephen C. Jacobsen, Salt Lake City, UT (US); John Lippert, Park City, UT (US); Clark C. Davis, Salt Lake City, UT (US); Kent Backman, Salt Lake City, UT (US)

(73) Assignee: SciMed Life Systems, Inc., Maple Grove, MN (US)

( * ) Notice: Subject to any disclaimer, the term of this patent is extended or adjusted under 35 U.S.C. 154(b) by 296 days.

(21) Appl. No.: 10/073,996

(22) Filed: Feb. 14, 2002

(65) Prior Publication Data

US 2002/0082499 A1 Jun. 27, 2002

Related U.S. Application Data

(60) Division of application No. 09/420,716, filed on Oct. 2, 1999, now Pat. No. 6,346,091, which is a continuation-in-part of application No. 09/023,806, filed on Feb. 13, 1998, now Pat. No. 6,022,369.

(51) Int. Cl.
*A61M 29/00* (2006.01)

(52) U.S. Cl. ...................................... 606/200
(58) Field of Classification Search ................. 606/200, 606/157, 194; 604/57, 508
See application file for complete search history.

(56) References Cited

U.S. PATENT DOCUMENTS

| | | |
|---|---|---|
| 4,994,069 A | 2/1991 | Ritchart et al. |
| 5,122,136 A | 6/1992 | Guglielmi et al. |
| 5,250,071 A | 10/1993 | Palermo |
| 5,261,916 A | 11/1993 | Engelson |
| 5,304,195 A | 4/1994 | Twyford, Jr. et al. |
| 5,350,397 A | 9/1994 | Palermo et al. |
| 5,354,295 A | 10/1994 | Guglielmi et al. |
| 5,427,118 A | 6/1995 | Nita et al. |
| 5,540,680 A | 7/1996 | Guglielmi et al. |
| 5,569,245 A | 10/1996 | Guglielmi et al. |
| 5,746,769 A | 5/1998 | Ton et al. |
| 5,749,894 A | 5/1998 | Engelson |
| 5,800,453 A | 9/1998 | Gia |
| 5,800,455 A | 9/1998 | Palermo et al. |
| 5,814,062 A | 9/1998 | Sepetka et al. |
| 5,851,206 A | 12/1998 | Guglielmi et al. |
| 5,855,578 A | 1/1999 | Guglielmi et al. |
| 5,891,128 A | 4/1999 | Gia et al. |
| 5,891,130 A | 4/1999 | Palermo et al. |
| 5,895,385 A | 4/1999 | Guglielmi et al. |
| 5,964,797 A | 10/1999 | Ho |
| 6,224,610 B1 | 5/2001 | Ferrera |

*Primary Examiner*—(Jackie) Tan-Uyen T. Ho
(74) *Attorney, Agent, or Firm*—Crompton, Seager & Tufte LLC (57) ABSTRACT

An apparatus includes an elongate wire (solid or hollow) having a distal end section for detachment and delivery to a target location, the wire also having a discontinuity located rearwardly of the distal end section for rupturing when vibrational energy is applied to the wire, and a vibrational energy source couples to the proximal end of the wire for selectively applying vibrational energy to the wire to travel to the discontinuity and causes detachment of the end section.

5 Claims, 6 Drawing Sheets

DETACHABLE COIL FOR ANEURYSM THERAPY

This application is a divisional of U.S. patent application Ser. No. 09/420,716 filed Oct. 10, 1999 U.S. Pat. No. 6,346,091 which is a continuation-in-part of application Ser. No. 09/023,806 which was filed on Feb. 13, 1998, now U.S. Pat. No. 6,022,369.

BACKGROUND OF THE INVENTION

1. Field of the Invention

The present invention relates to endovascular devices for occluding and/or stabilizing and sealing off vasculature or body passageways, tissue defects, and aneurysms. More specifically, the present invention relates to a method and apparatus for threading wires into body cavities and detaching end sections thereof using vibrational energy, for example, in the form of elastic waves.

2. State of the Art

A variety of methods have been developed for occluding and/or stabilizing and sealing off vasculature or body passageways tissue defects and aneurysms with the use of endovascular catheters including injectable particles, injectable glue, and detachable coils and other devices. The use of detachable coils appears to be gaining widest acceptance for aneurysm therapy, perhaps because of the ease and precision of control of the delivery and disposition of the coil at the desired occlusion site.

One approach for delivering and detaching coils at an occlusion site involves forming or attaching the coil at the distal end of a wire, and then threading the coil and wire through a catheter until the coil is disposed at the occlusion site. An electric current is then applied to the proximal end of the wire and conducted through the wire to the point of origin or attachment of the coil where it causes the coil, for example, by electrolysis, to detach from the wire. See U.S. Pat. Nos. 5,569,245, 5,624,449, 5,122,136, 5,540,680, and 5,354,295.

Among the problems associated with the electrically detachable coil approach is the time necessary to effectuate detachment (which changes with increasing number of devices delivered), the lack of reliability that the coil will detach, discomfort with the use of a grounding needle (insertable in the flesh of the patient) required for the proper functioning of the device, generation of particulates from the detachment site (electrolysis), and inability to select the size of the coil in vivo.

OBJECTS AND SUMMARY OF THE INVENTION

It is therefore an object of the invention to provide an apparatus and method for selectively detaching an end section of a wire in a body passageway by non-electrical means.

It is another object of the invention to provide such an apparatus and method in which the end section of the wire may be quickly and reliably detached, independently of the number of devices delivered.

It is a further object of the invention to provide such an apparatus and method in which little discomfort results to the patient.

It is still another object of the invention to provide such an apparatus and method, in accordance with one aspect thereof, in which multiple sections of the end segment of the wire may each be selectively detached at different times.

It is an additional object of the invention to provide such an apparatus and method, in accordance with another aspect thereof, in which it may readily be determined by the user when the end section of the wire has detached.

It is a further object of the invention to provide such an apparatus and method in which little preparation of the wire and end section is required to allow for subsequent use and detachment of the end segment.

It is still another object of the invention to provide such an apparatus and method in which therapeutic fluid may be delivered along with the wire to a target body location.

The above and other objects of the invention are realized in a specific illustrative embodiment of a wire apparatus with a detachable distal end which includes an elongate wire (either solid or hollow) having a distal end section, and a discontinuity located rearwardly of the distal end section for rupturing when vibrational energy is applied thereto. The apparatus includes a delivery means coupled to the elongate wire for delivering therapeutic fluid to a target body location and a vibrational energy generator, preferably an ultrasound generator, for applying vibrational energy to the wire to travel to the discontinuity to cause detachment of the distal end section. The vibrational energy may comprise axial or torsional waves mechanically induced into the wire.

In use, the wire is threaded through a vasculature or body passageway to a target location, and therapeutic fluid is injected through a catheter or hollow wire to the target location. Then vibrational energy is applied to the wire to cause the distal end section to detach and remain at the target location to occlude the passageway, and the remainder of the wire is withdrawn from the patient.

In accordance with one aspect of the invention, the discontinuity could include a cut in the wire, a hole, a reduced diameter section, an abrupt increase in mass, an adhesive, soldered or spot-welded joint which joins the distal end section to the wire, a coil soldered or adhesively attached to either the outer surface of a solid or hollow wire, or to the inner surface of a hollow wire, or a heat or chemically treated section. Alternatively, the distal end section could include a plurality of discontinuities, each adapted to rupture at a different vibrational levels or frequencies, to detach a selected portion of the distal end section which is distal to the discontinuity being ruptured.

Other objects, features and advantages of the invention will become apparent from a consideration of the following detailed description presented in connection with the accompanying drawings

DETAILED DESCRIPTION OF THE PREFERRED EMBODIMENT

Reference will now be made to the drawings in which the various elements of the present invention will be given numeral designations and in which the invention will be discussed so as to enable one skilled in the art to make and use the invention.

Figure 1:
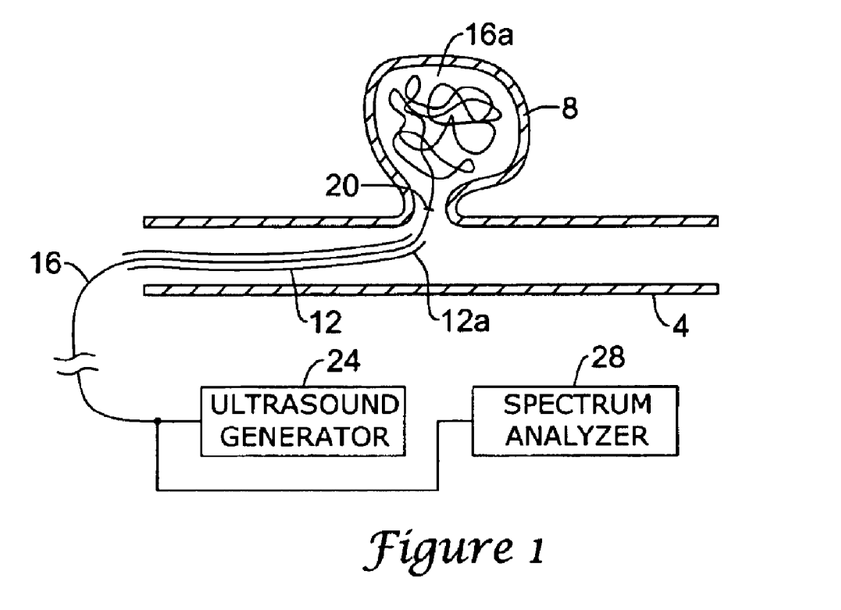
FIG. 1 shows a side, fragmented, cross-sectional view of a wire made in accordance with the principles of the present invention, in which the proximal end of the wire is coupled to an ultrasound generator and the distal end of the wire is formed into a tangled mass disposed in an aneurysm.

Referring to FIG. 1, there is shown a side, cross-sectional view of a blood vessel 4 in which an aneurysm 8 is shown formed in one side of the vessel. A fragmented view of a catheter 12 is shown threaded in the vessel 4, with a terminal end 12a positioned adjacent the aneurysm 8. Threaded through the catheter 12 is a wire 16, which extends entirely through the catheter 12 and out the terminal end 12a into the aneurysm 8 (or the entrance thereof) to substantially fill the aneurysm with a coiled end section 16a. Wire 16 may be any long prismatic element, whether solid or hollow, and the end section 16a could be tangled, formed into specific shapes, etc. as well as being coiled.

A discontinuity 20 is formed between the end section 16a of the wire and the rest of the wire 16. The discontinuity 20 may take a variety of shapes and forms, so long as it is designed to rupture, break or separate when vibrational energy of a certain frequency and magnitude is applied to the wire 16. The vibrational energy source in the FIG. 1 embodiment is preferably an ultrasound generator 24, but could be something as simple as a striker, mallet, hammer, etc. for striking the wire 16 to cause mechanical vibrations to propagate to the discontinuity 20.

In use, the catheter 12 is threaded through a vasculature or body passageway to a site at which the end section 16a of the wire is to be disposed, such as the aneurysm 8 in FIG. 1. The purpose of such disposal, for example, is to provide an occlusion in the passageway to allow for coagulation of blood to prevent further flow, or, as in the FIG. 1 schematic, to cause scarring in the aneurysm 8 to thereby fill the aneurysm with scar tissue to prevent the bursting thereof, etc. The end section 16a is shown as being coiled or tangled but when threaded through the catheter 12 it would be straightened. Formation of a wire or coil with these properties is frequently accomplished by heat treating or other methods known in the art. Then when the end section 16a is pushed out the terminal end 12a of the catheter, the end section would resume the normally coiled or tangled condition as shown (enhanced also by body warmth).

After the end section 16a has been guided to the desired target site, the ultrasound generator 24 would be connected to the proximal end of the wire 16 and an ultrasound signal applied thereto. The frequency and amplitude of the signal (observed on a spectrum analyzer 28) would be selected to produce high stress in the discontinuity 20, fatiguing the wire so that it breaks, ruptures, or otherwise separates at the discontinuity, leaving the end section 16a in the aneurysm 8. Because the system uses vibrations in the ultrasonic range, the separation is accomplished rapidly, reliably and without pain to the subject. A more detailed diagram of the vibrational energy system and method are provided in FIG. 15A, described below.

Figure 2:
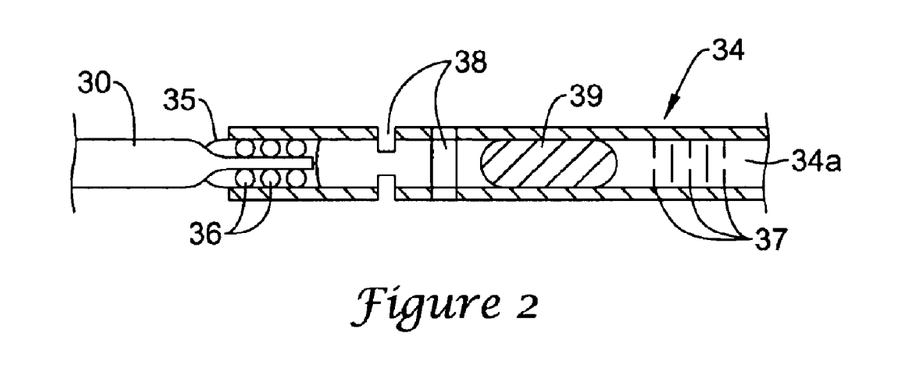
FIGS. 2–3, 4A–4C, and 5–6 show side, fragmented views of different embodiments for providing discontinuities to allow detachment of end coil sections from delivery wires, all in accordance with the principles of the present invention.

FIG. 2 shows a fragmented, side, cross-sectional view of a wire 30 made, for example, of stainless steel, connected to a tubular end section 34 made, for example, of nickel titanium alloy or platinum. The terminal end of the wire 30 is tapered, as shown, and is inserted into a hollow 34a in the proximal end of the end section 34, and there secured by an adhesive, solder, or weld 35. A coil 36 made, for example, of stainless steel is soldered, welded or otherwise attached to the terminal end of the wire 30 to enhance the bond between the wire and the end section 34.

The end section 34 includes a plurality of cuts 37 made to extend generally transversely in the end section and provided to shape the end section into a coiled or tangled configuration, and to allow for more surface area exposure of the end section to blood for inducing clotting. See co-pending U.S. patent application Ser. No. 08/568,493, filed Dec. 7, 1995, for a further discussion of the employment of cuts in wire to allow flexibility and control shape while maintaining torquability. Two or more cuts 38 (rotated 90 degrees with respect to one another) are shown spaced rearwardly from the plurality of cuts 37 by a distance greater than the spacing between the cuts 37, and are provided to serve as the discontinuity for rupturing (through fatigue) when the vibrational signal is applied to the wire 30. The cuts 38, of course, could be formed at the same time as the other cuts 37 but, for example, would be made deeper (creating a thinner beam), wider (creating a longer beam), or adjacent a mass 39 disposed in the end section 34, or a combination of these, to sever or rupture when the vibrational signal is applied to the wire 30.

Figure 3:
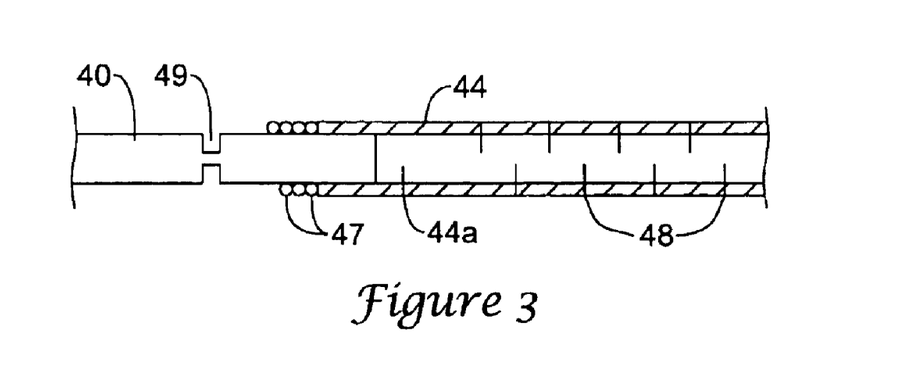

FIG. 3 shows a fragmented, side, cross-sectional view of another embodiment of a wire with a discontinuity in accordance with the present invention. Here, a wire 40 made, for example, of stainless steel, is fitted into the hollow 44a of an end section 44 made, for example, of nickel-titanium alloy. The wire 40 would be held in place in the hollow by a suitable adhesive, such as epoxy or cyanoacrylate. A plurality of cuts 48 are made in the end section 44 to provide for coiling and shaping the end section as desired for ultimate disposition at a target site in a body passageway. A cut or diameter reduction 49 is also formed in the wire 40 to provide the desired discontinuity. A coil mass 47 might also be added about the wire 40 to further exaggerate the discontinuity. The cut 49 might advantageously be about ½ of the way through the wire 40 in the transverse direction to serve to rupture or separate when an ultrasound signal is applied to the wire.

Figure 4A:
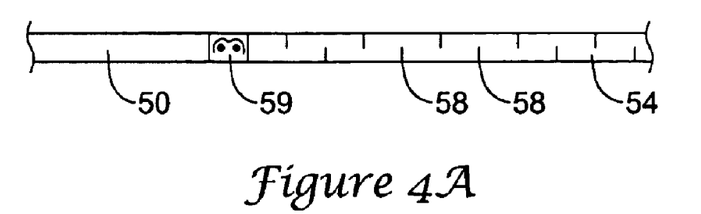

FIG. 4A shows another embodiment of a discontinuity between a wire 50 and an end section 54, again including cuts 58. The terminal end of the wire 50 is attached by a section of adhesive 59 to the proximal end of the end section 54. The adhesive 59 is selected from materials that are somewhat brittle, such as sodium silicate, so that when an ultrasound signal is applied to the wire 50, the adhesive 59 will fracture to allow the end section 54 to separate from the wire 50. Alternatively, section 59 of wire 50 could be heat-treated or H+ embrittled to make the wire brittle at that location. As yet another alternative, section 59 could be chemically-treated, such as by etching, to make the wire weaker at that location.

Figure 4B:
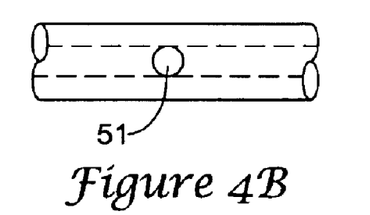
Figure 4C:
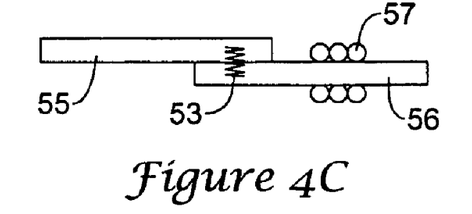

FIG. 4B shows the discontinuity formed as a hole 51, whereas FIG. 4C shows the discontinuity as a spot weld 53 joining the wire 55 side-by-side to an end section 56. A coil mass 57 provides additional discontinuity. The process of spot welding heats the wire 55, making it more susceptible to fatigue and breaking. In fact, heating alone may be used to create a "discontinuity".

Figure 5:
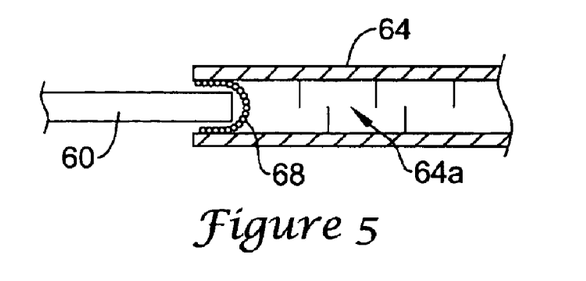

FIG. 5 shows an embodiment similar to that of FIG. 3 except that the discontinuity does not comprise a cut in either the wire 60 or end section 64. Rather, the discontinuity is formed at the joint or connection between the wire 60 and end section 64 wherein the wire is inserted in the hollow 64a of the end section and held in place by a blood soluble adhesive 68, such as sodium silicate. When the end section 64 is guided through a blood vessel by the wire 60 (i.e., through a catheter inserted in a blood vessel), blood enters the hollow 64a of the end section 64 which, along with blood contacting the adhesive 68 at the proximal end of the end section, operates to dissolve the adhesive and allow separation of the end section from the wire.

Application of a vibrational signal such as an ultrasound signal to the wire 60 accelerates the dissolution and ultimate separation of the end section 64 from the wire 60 to allow disposition of the end section at the target site. In effect, two mechanisms may be employed to cause separation—providing greater security and safety in ensuring separation.

Figure 6:
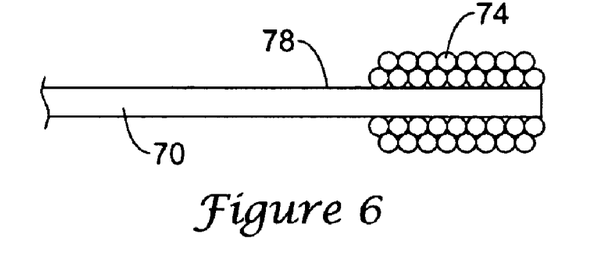

The FIG. 6 embodiment includes a wire 70 at the distal end of which is disposed a heavy mass of material 74, preferably wound about the distal end. For example the mass 74 might include windings of platinum. The abrupt transition from the wire 70 to the heavy mass 74 provides a discontinuity at location 78 just behind the mass so that when vibrational energy of a certain frequency and amplitude is applied to the wire, the wire is caused to break at the discontinuity or stress point 78, releasing the mass 74 at a target site in a body passageway. The wire 70 might also be made of platinum, stainless steel or nickel titanium alloy.

Figure 7:
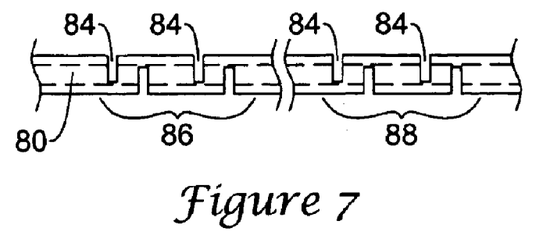
FIG. 7 is a side, fragmented view of a hollow end coil section having a plurality of discontinuities for tuned resonator detachment, in accordance with the principles of the present invention.

FIG. 7 shows an embodiment of a detachable wire 80 having a plurality of longitudinally spaced cuts 84 in sections 86 and 88, which act as separate discontinuities. Each of the discontinuities 84 of section 86 are formed or "tuned" with a predetermined depth, width, and/or spacing to rupture in response to different amplitudes and frequencies of vibrational energy than the discontinuities of section 88. In this manner, the user can selectively apply vibrational energy to the wire 80 to cause a selected section of the discontinuities 84 to rupture. Such rupturing can take place successively to deposit lengths of wire at different locations in a body passageway or to deposit all of the lengths (to serve as emboli) at a single location. The "tuning" of the discontinuities 84 is both a function of the characteristics of the cuts, and also of the segment lengths between the discontinuities. Such timing could be used to "deposit" great numbers of particles such as for AVM therapy.

The ultrasonic vibrational energy can be transmitted down the wire in two different modes of propagation: axial or torsional. In the axial mode, the wire is alternately placed in tension and compression along the axis of the wire as the wave travels. In the torsional transmission mode, the wire is alternately placed in clockwise and counterclockwise torsion about its axis as the wave travels. Both modes are useful.

The detachment sites shown and described above are configured for detachment in the axial mode. However, torsional waves are advantageous when using a section of wire which has been provided with cuts to enhance its lateral flexibility. The cuts severely reduce the axial stiffness of the wire (particularly of hollow wire), but can be made in such a way as to not reduce the torsional stiffness of the wire as much. (See, e.g. U.S. patent application Ser. No. 08/568,493, filed Dec. 7, 1995). The cut wire therefore is more capable of transmission of torsional than of axial vibration. Where selective detachment is desired, the wave is required to travel through sections of cut wire to reach the various detachment sites. Consequently, the torsion mode is preferred for selective detachment of cut wire.

The cuts 84 create spring elements to isolate the intermediate uncut sections of the wire 80 which have a mass. When a vibrational energy wave at the resonant frequency of the spring/mass system is applied to the wire 80, the wire is excited longitudinally and the sections of mass between the cuts vibrate longitudinally at high amplitude which fatigues the spring elements (location of cuts) causing them to break. The wire 80 could advantageously be made of stainless steel or nickel titanium alloy.

Figure 8:
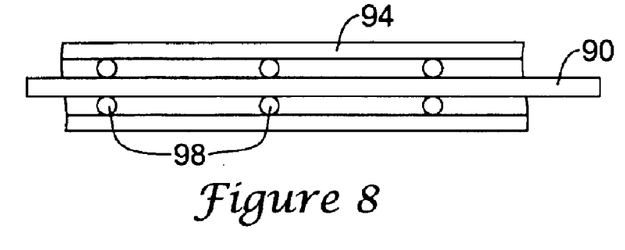
FIGS. 8 and 9 show side, fragmented views of embodiments of guide wire/catheter combinations where friction between the guide wire and catheter is minimized.
Figure 9:
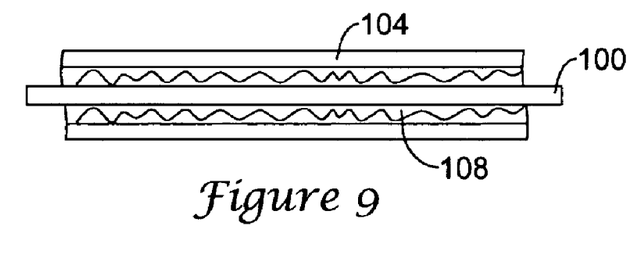

FIGS. 8 and 9 show side, cross-sectional, fragmented views of a type of wave guide construction for transmitting vibrational energy along a wire surrounded by a catheter or sleeve. Referring to FIG. 8, there is shown a wire 90 disposed inside of a catheter or sleeve 94 but held out of touch from the sleeve by supports, for example, in the form of rings spaced apart longitudinally and uniformly along the length of the wire and sleeve. The supports 98 are positioned at the velocity nodal points of the vibrational energy waves which are transmitted along the wire/sleeve combination to cause detachment of an end section (not shown). The velocity nodal points, of course, are those locations in a mechanical wave where there is little or no movement or velocity of the wave-carrying structure, whereas the locations midway between the supports 98 are the antinodes where there is maximum movement of the wave-carrying structure. By providing the supports 98, the wire and sleeve are held apart to thereby prevent friction between the two as the vibrational energy wave travels down the wire/sleeve combination. Thus, little energy is lost along the length of the wire and sleeve and so detachment of the end section would take less time.

FIG. 9 is a side, cross-sectional, fragmented view of a wire 100 about which is disposed a sleeve 104 and between which is disposed a hydrophillic coating, elastomeric material, or lubricant 108 to allow the wire and sleeve to move relative to one another without significant friction and thus without loss of vibrational energy.

Figure 10:
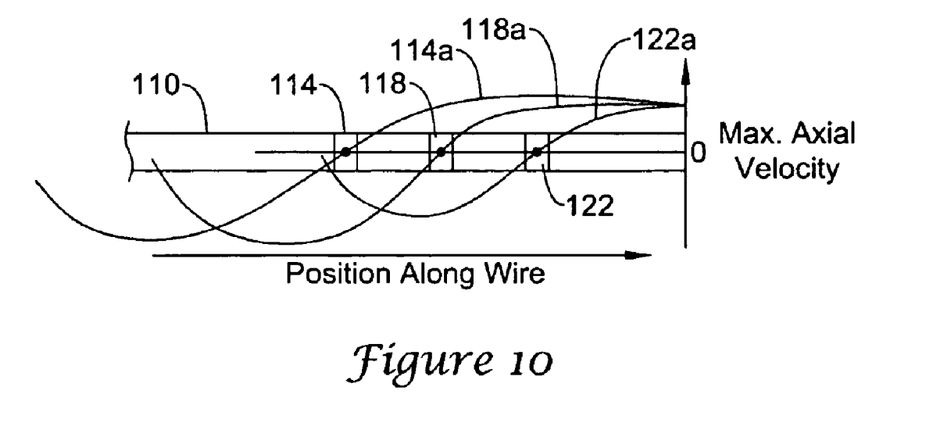
FIG. 10 is a graphic view of a wire illustrating nodal points responsive to different vibrational frequencies for detachment of end sections.

FIG. 10 shows a graphic representation of a wire 110 having discontinuities 114, 118 and 122 spaced longitudinally along the wire. Graphically superimposed over the wire 110 are three vibrational energy waves 114a, 118a, and 122a. In order to cause the wire 110 to separate at one of the selected discontinuities, a vibrational energy wave is applied to the wire so that the nodal point of the wave falls at the desired discontinuity. A vibrational energy wave causes mechanical resonance in the longitudinal direction where nodal points fall at locations which are spaced every one half of the wavelength. As briefly mentioned earlier, at the nodal points along the wire, the velocity or movement of the wire is minimal, but the stress is maximal. Consequently, by applying a vibrational energy wave such as wave 114a to the wire 110, the wire would be caused to separate at that location where the greatest stress is occurring and the wire is weakest, because a nodal point of wave 114a occurs at discontinuity 114. Similarly, if it were desired that the separation occur at discontinuity 118, then vibrational energy wave 118a would be applied to the wire, etc. In the manner described, appropriate mechanical energy waves can be applied to wires to cause separation at selected discontinuities along the wire. The various embodiments described above can be used to occlude blood flow, create scar tissue in aneurysms, in a known manner, or the embodiments could also be used to detach any type of end section device, such as a tubal block; in a body passageway, for example, a fallopian tube; to block passage of eggs; or detach elements containing drugs for delivery to a target site; etc. That is, the embodiments are not limited solely to use in vasculature passageways.

Figure 11A:
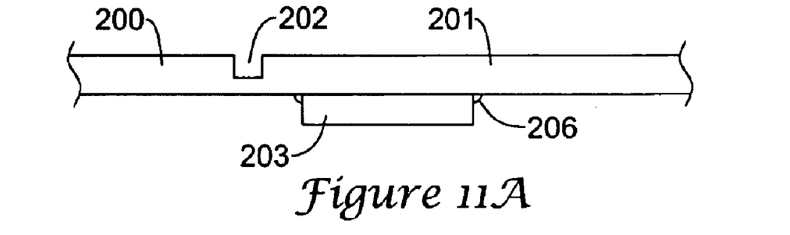
FIGS. 11A–11C show side views of different embodiments of the invention having a hollow wire and a mass or group of masses disposed on adjacent or opposite sides of a cut in the hollow wire.

FIG. 11A shows a side view of another embodiment of a wire with a discontinuity in accordance with the present invention. Here, a wire 200, made, for example, of stainless steel, is hollow, allowing therapeutic fluid and drugs to pass therethrough. A plurality of cuts (not shown) may be made in the end section 201 to provide for coiling and configuring the end section as desired for ultimate disposition at a target site in a body passageway. A cut or diameter reduction 202 is also formed in the hollow wire 200 to provide the desired discontinuity. A bottom mass 203 is added below the cut with an adhesive 206 to further exaggerate the discontinuity. The bottom mass 203 is preferably made of platinum.

Figure 11B:
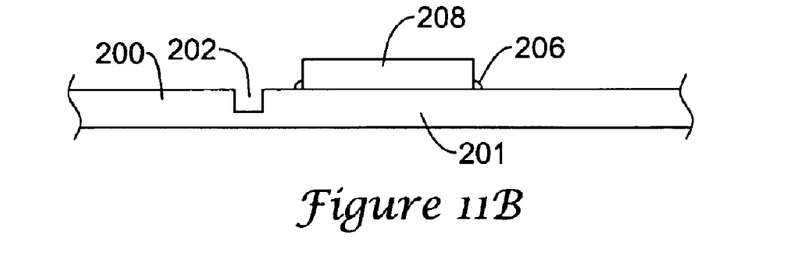

FIG. 11B shows a side view of another embodiment of a wire with a discontinuity similar to FIG. 11A. This embodiment has a top mass 208 added adjacent to the cut 202 with an adhesive 206 to further exaggerate the discontinuity. The top mass 208 is preferably made of platinum, and the adhesive 206 can be epoxy or cyanoacrylate. Alternatively, the mass may be affixed by a welded or soldered connection.

Figure 11C:
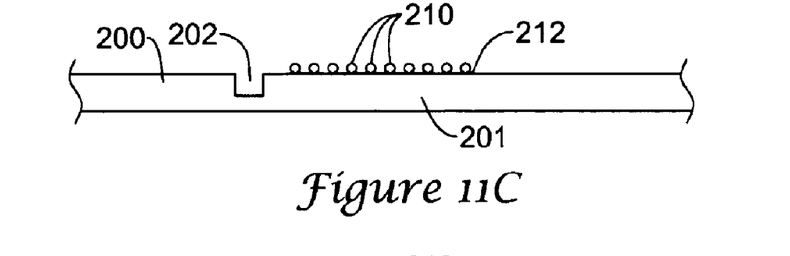

FIG. 11C is a side view of a hollow wire 200 made, for example, of stainless steel, to allow therapeutic fluid or drugs to pass through to a target body site. A plurality of top masses 210 are attached adjacent to the cut 202 with an adhesive 212 to further exaggerate the discontinuity. The plurality of masses 210 are preferably made of platinum. It will be apparent that the wire of FIG. 11C could be alternatively formed with a plurality of bottom masses attached below the cut 202 in the hollow wire 200, in the manner of FIG. 11A.

Figure 12A:
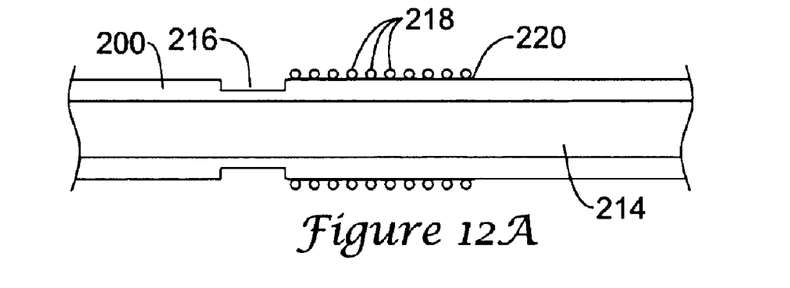
FIGS. 12A–12B show sectional views of different embodiments of a hollow wire with a coil mass disposed adjacent a cut in the wire that does not extend entirely through the outer wall of the wire.
Figure 12B:
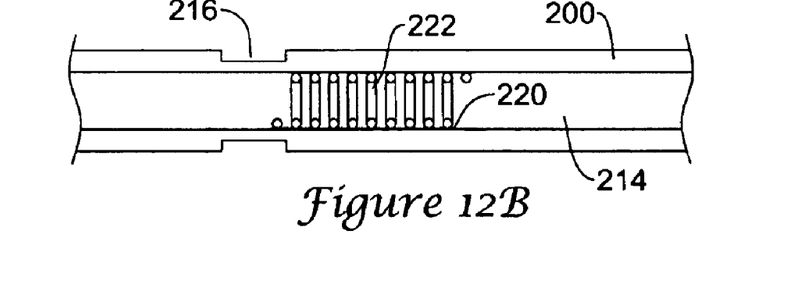

The hollow wire can also be formed without through-cuts to provide a hollow detachment site that does not allow fluids to escape from the lumen of the hollow wire. As shown in FIG. 12A, a hollow wire 200 with a central lumen 214 is formed with an annular cut 216, or alternatively a pair of oppositely disposed straight cuts, forming a discontinuity, that does not extend to the lumen. A coil 218 which wraps around the outside of wire 200 is disposed adjacent cut 216 and attached with adhesive 220, to exaggerate the effect of the discontinuity. Alternatively, as shown in FIG. 12B, a coil 222 may be disposed within lumen 214 of the wire, adjacent the cut 216.

Figure 13:
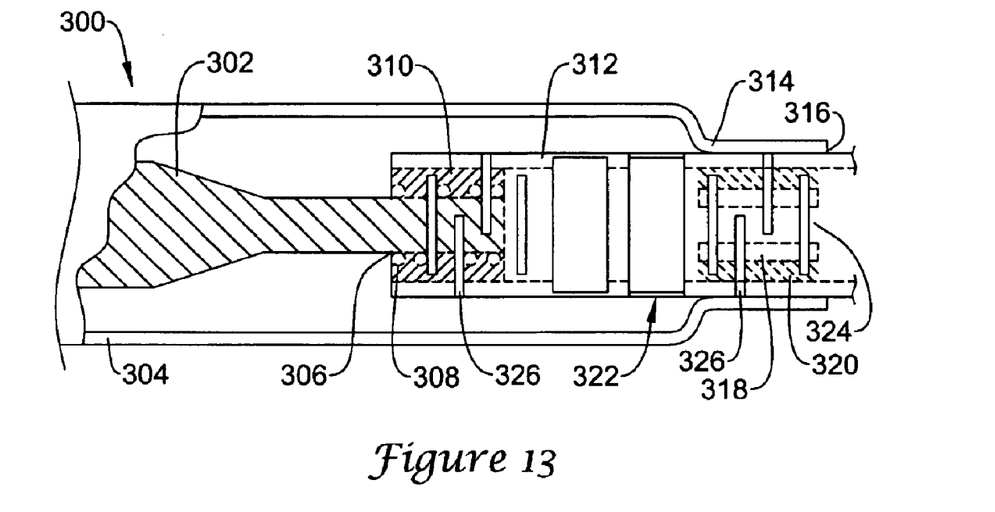
FIG. 13 shows a cut-away view of a catheter and guide wire combination with a wide cut to allow fluid to pass through the slot and out the distal end.

FIG. 13 is a side cut away view of a catheter 304 and guide wire combination 302 with a wide cut 322 to allow therapeutic fluid to pass through a fluid passage 324 and into a target body location. The cuts 322 are wide to provide lateral flexibility of the detachment site so that it can be threaded through tortuous anatomy without damage. The guide wire 302 is made, for example, of stainless steel, connected to a tubular distal end section 312 made, for example, of nickel titanium alloy or platinum. The terminal end of the wire 302 is tapered, as shown, and is inserted into the proximal side of the end section 312, and there secured by an adhesive 310. A coil 308 made, for example, of stainless steel is soldered 306 or otherwise attached to the terminal end of the wire 302 to enhance the bond between the wire 302 and the end section 312.

The end section 312 includes a plurality of cuts 326 formed generally transversely in the end section 312. Cuts 326 are configured to impart flexibility and to shape the end section 312 into a coiled or tangled configuration. Two or more wide cuts 322 are shown spaced from the plurality of cuts 326 by a distance greater than the spacing between the cuts 326, and are provided to serve as the discontinuity for rupturing or fatigue when a vibrational signal is applied to the wire 302. The cuts 322 of course, could be formed at the same time the other cuts 326 are being formed but, would be made deeper or wider, to sever or rupture when the vibrational signal is applied to the wire 302.

Figure 14:
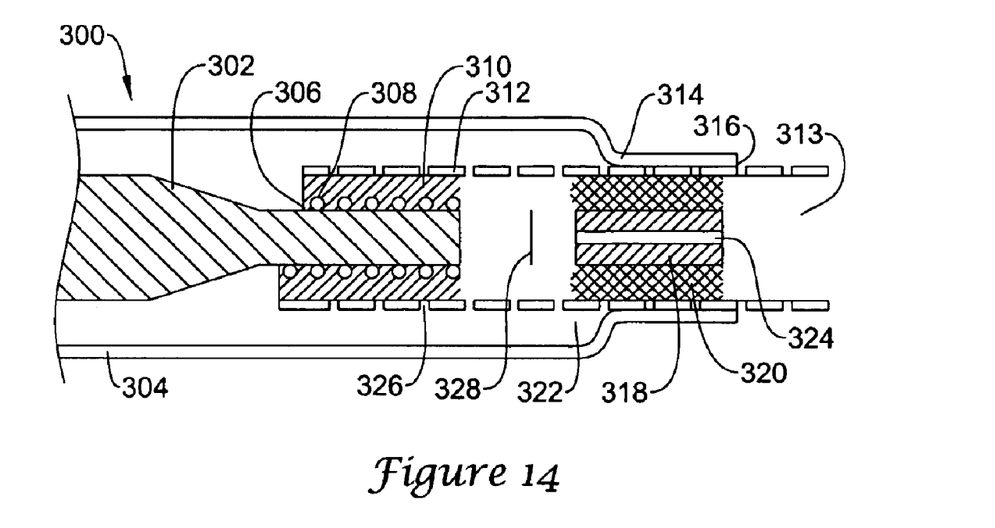
FIG. 14 is a cross-section view of the catheter and guide wire combination showing the adhesive joint between the guide wire and the distal end of the wire and the fluid passage through the mass in the distal end.

FIG. 14 is a side cross sectional view of the catheter 304 and guide wire 302 combination with a wide cut 322 to allow fluid to pass through the cuts 322 and out the hollow distal end section 312. The terminal end of the wire 302 is tapered and inserted into the distal end section 312 at the proximal side of the end section 312, and secured by an adhesive 310. A coil 308 is soldered 306 or otherwise attached to the terminal end of the wire 302 and functions as a mechanical interlock for the adhesive bond 310 between the wire 302 and the end section 312. A plurality of cuts 326 are formed in the end section 312 extending generally transversely to shape the end section into a coiled or tangled configuration. Two or more cuts 322 are shown spaced from the plurality of cuts 326 by a distance greater than the spacing between the cuts 326, and are provided to serve as the discontinuity for rupturing when a vibrational signal is applied to the wire 302. A fatigue area 328 shown in FIG. 14 ruptures when high-frequency mechanical or ultrasonic energy passes through it.

Therapeutic fluid is delivered to a target body location through the catheter 304. The fluid passes through the catheter 304 and into the wide cuts 322. The therapeutic fluid is retained within the catheter 304 due to the slip fit of the catheter containment sleeve 314 just past the wide cuts 322. A fluid passage 324 is formed between the platinum masses 318 in the end section 312 to allow fluid to flow out the distal end 313. The platinum masses 318 are attached to the inside of the distal end 312 with an adhesive 320. Upon completion of the site specific fluid or drug delivery, an ultrasonic transducer is used to fatigue the wide cut 322. Upon the localized fracture of the wide cut 322, the delivery section of the device 300 can be removed. The catheter containment sleeve 314 slides off the wire end 313 via a hydrophilic interface 316, and this leaves the wire end 313 inside the body. The catheter 304 and the guide wire 302 are then removed.

Naturally, it will be desirable for a user of this invention to know immediately when the end section of a wire has been detached from the wire so that the wire can be withdrawn from the body passageway. For each of the embodiments described above involving a delivery wire portion and an end section for ultimate detachment at a target site, the combinations of wire and end sections all have natural or resonant frequencies. Thus, when vibrational energy is applied to a wire, such as wire 16 in FIG. 1, the resonant frequency of the combination of the wire 16 and end section 16a will have a certain resonant frequency which can be detected by conventional spectrum analysis methods.

Figure 15A:
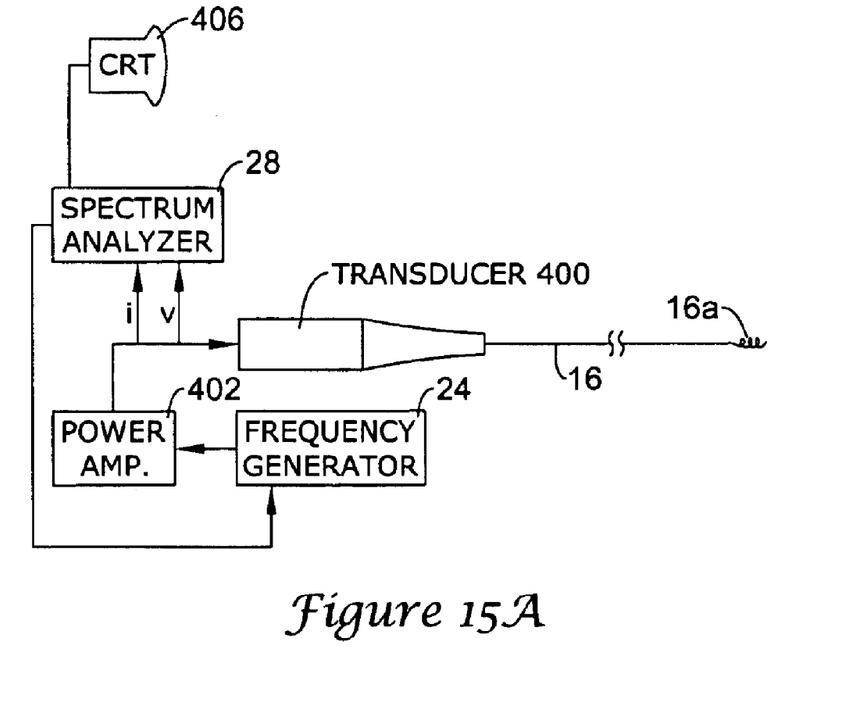
FIG. 15A depicts a system for determining when detachment of the distal end has occurred.

FIG. 15A depicts a system for monitoring and displaying this resonant frequency, and for determining when detachment has occurred. This system shown in FIG. 15A is consistent with, but more detailed than that shown in FIG. 1. The system generally comprises an ultrasonic transducer 400 connected to a detachable coil device 16 having a detachable end section 16a, a spectrum analyzer 28, a frequency generator 24, and a power amplifier 402. The ultrasonic transducer 400 is driven with a periodic waveform produced by the frequency generator 24 and amplified by the power amplifier 402. The electrical impedance, z (a complex ratio of voltage to current flow) of the transducer is a function of frequency, and of the physical device driven by the transducer (the detachable coil device 16). The impedance of the transducer is measured by the spectrum analyzer 28 as shown, or alternatively, may be measured by any other suitable electronic device, such as a microcontroller which is made for that purpose.

Figure 15B:
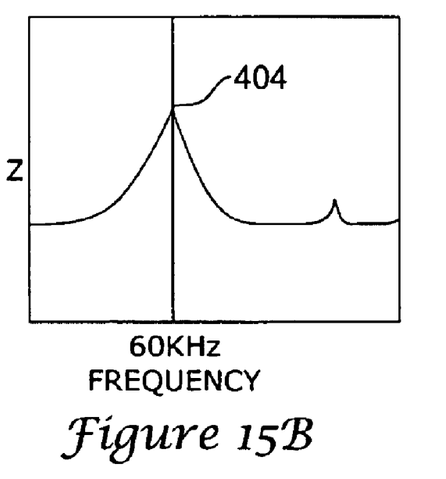
FIGS. 15B and 15C show a plot of impedance (z) versus frequency before and after detachment, respectively.
Figure 15C:
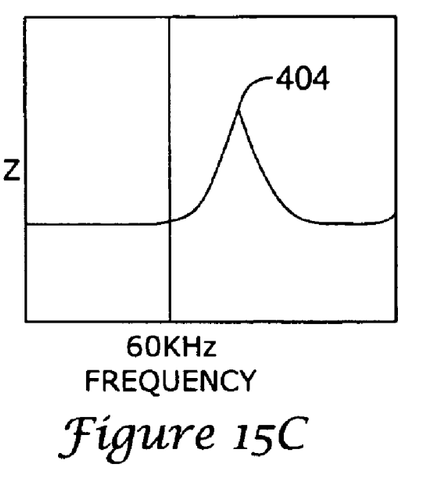

The spectrum analyzer 28 sweeps the frequency input to the transducer 400 while measuring the voltage v and current i to the transducer to generate a plot of impedance z versus frequency, which is displayed on a CRT screen 406 associated with the spectrum analyzer. Two exemplary plots of impedance versus frequency are given in FIGS. 15B and 15C as they would appear on CRT screen 406. These plots show impedance (z) versus frequency before and after detachment, respectively. It will be apparent that the plot of impedance versus frequency exhibits resonant peaks. As shown in FIG. 15B, when the coil device is unaltered, it may exhibit a resonant peak 404 at 60 KHz, for example. However, when the physical nature of the load on the transducer changes, i.e. the coil detaches, the resonant peak 404 shifts to the right of 60 KHz as shown in FIG. 15C.

Consequently, by observing the resonant frequency display on the analyzer 28, a user can obtain instantaneous information as to when the end section 16a has detached from the wire device 16. As an alternative or addition to visual observation of the impedance versus frequency plot, an indicator lamp, and audible alarm, a secondary indication on the CRT screen, or any other means of providing a discernable signal to the user could be employed which would create a discernable signal only when detachment occurs.

In the manner described, a method and apparatus have been provided by which an end section of a wire may be easily, reliably and quickly detached from the delivery portion of the wire, generally without pain to the subject. The detached end section may be in the form of a coil, mass or other device and may be deposited in vasculature passageways or other body passageways. Vibrational energy is used to rupture discontinuities separating the delivery portion of the wire from the end section and so no electrical current of any kind is required, making it much safer for the subject.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A medical device comprising an elongate wire having a distal end section configured for delivery to and detachment at a target body location, said wire comprising a discontinuity located proximal to said distal end section, said discontinuity being configured to rupture when vibrational energy is applied to said wire, the medical device further comprising a catheter extending at least to said discontinuity and proximal therefrom and a vibrational energy source connected to the elongate wire for causing mechanical vibrations to rupture the discontinuity.

2. A medical device comprising an elongate wire having a distal end section configured for delivery to and detachment at a target body location, said wire comprising a discontinuity located proximal to said distal end section, said discontinuity being configured to rupture when vibrational energy is applied to said wire, the medical device further comprising a catheter, at least part of said wire being solid and being located inside said catheter, said wire being connected to a slotted tubular member extending distal from said wire and distal from said catheter, at least part of said tubular member forming said distal end section and a vibrational energy source connected to the elongate wire for causing mechanical vibrations to rupture the discontinuity.

3. The medical device of claim 2 configured to deliver a fluid through said catheter, through at least some of said slots, and through at least part of said tubular member.

4. The medical device of claim 2, said discontinuity comprising at least one slot formed in said tubular member.

5. The medical device of claim 2, wherein the catheter extends at least to said discontinuity and proximal therefrom.

* * * * *